US011975155B2

(12) United States Patent
Garcia Molina

(10) Patent No.: US 11,975,155 B2
(45) Date of Patent: May 7, 2024

(54) METHOD TO PREDICT THE SLOW-WAVE RESPONSE

(71) Applicant: KONINKLIJKE PHILIPS N.V., Eindhoven (NL)

(72) Inventor: Gary Nelson Garcia Molina, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 665 days.

(21) Appl. No.: 17/091,036

(22) Filed: Nov. 6, 2020

(65) Prior Publication Data

US 2021/0138185 A1 May 13, 2021

Related U.S. Application Data

(60) Provisional application No. 62/933,727, filed on Nov. 11, 2019.

(51) Int. Cl.
*A61M 21/02* (2006.01)
*A61B 5/00* (2006.01)
(Continued)

(52) U.S. Cl.
CPC ............ *A61M 21/02* (2013.01); *A61B 5/369* (2021.01); *A61B 5/4812* (2013.01);
(Continued)

(58) Field of Classification Search
CPC .......... A61M 21/02; A61M 2021/0022; A61M 2021/0027; A61M 2021/0044;
(Continued)

(56) References Cited

U.S. PATENT DOCUMENTS

2016/0082222 A1* 3/2016 Garcia Molina ...... A61B 5/375
600/27
2017/0340854 A1* 11/2017 Geerlings ............ A61B 5/4812

FOREIGN PATENT DOCUMENTS

WO 2018104163 A1 6/2018

OTHER PUBLICATIONS

Bresch, E. et al., "Recurrent Deep Neural Networks for Real-Time Sleep Stage Classification From Single Channel EEG", Front. Comput. Neurosci., Oct. 16, 2018.
(Continued)

*Primary Examiner* — Thaddeus B Cox
*Assistant Examiner* — Joshua Daryl D Lannu

(57) ABSTRACT

The present disclosure pertains to automatically predicting a slow wave response of a subject to sensory stimulation during a sleep session. The sensory stimulation may be delivered to the subject upon detection of deep NREM sleep. The sensory stimulation may be auditory, haptic, visual, or other stimulation. The system delivers stimulation to the subject in blocks of stimulation separated from one another be intra-block intervals. The blocks are separated from each other by inter-block stimulations. The system compares the stimulated slow wave activity of the subject to the unstimulated slow wave activity of the subject. The system may update the stimulation parameters based on the comparison and deliver a subsequent block stimulation. Once the comparison indicates that the stimulated slow wave activity is significantly different from the unstimulated slow wave activity, the system may apply continuous fixed sensory stimulation to the user according to the most recent stimulation parameters.

26 Claims, 7 Drawing Sheets

(51) Int. Cl.
*A61B 5/369* (2021.01)
*A61M 21/00* (2006.01)

(52) U.S. Cl.
CPC ... *A61B 5/6803* (2013.01); *A61M 2021/0022* (2013.01); *A61M 2021/0027* (2013.01); *A61M 2021/0044* (2013.01); *A61M 2205/50* (2013.01)

(58) Field of Classification Search
CPC ...... A61M 2205/50; A61M 2021/0016; A61M 2205/3375; A61M 2205/3561; A61M 2205/3592; A61M 2209/088; A61M 2230/06; A61M 2230/10; A61M 2230/42; A61B 5/369; A61B 5/4812; A61B 5/6803; A61B 5/4836; A61B 5/02055; A61B 5/08; A61B 5/7264

See application file for complete search history.

(56) References Cited

OTHER PUBLICATIONS

H.-V. V Ngo, T. Martinetz, J. Born, and M. Molle, "Auditory Closed-Loop Stimulation of the Sleep Slow Oscillation Enhances Memory," Neuron, vol. 78, no. May, pp. 1-9, 2013.

N. A. Papalambros, G. Santostasi, R. G. Malkani, R. Braun, S. Weintraub, K. A. Paller, and P. C. Zee, "Acoustic enhancement of sleep slow oscillations and concomitant memory improvement in older adults," Front. Hum. Neurosci., vol. 11, no. March, pp. 1-14, 2017.

L. Besedovsky, H.-V. V Ngo, S. Dimitrov, C. Gassenmaier, R. Lehmann, and J. Born, "Auditory closed-loop stimulation of EEG slow oscillations strengthens sleep and signs of its immune-supportive function," Nat. Commun., vol. 8, No. 1, p. 1984, 2017.

M. M. Leminen, J. Virkkala, E. Saure, T. Paajanen, P. C. Zee, and G. Santostasi, "Enhanced Memory Consolidation Via Automatic Sound Stimulation During Non-REM Sleep," Sleep, vol. 40, No. 3, pp. 1-10, 2017.

C. Diep, S. Ftouni, S. Drummond, and C. Anderson, "Enhancing Slow Wave Activity Via an Automated Phase Locked Acoustic Stimulation," in SLEEP 2017, 31st Annual Meeting of the Associated Professional Sleep Societies (APSS), 2017, p. A301.

M. Bellesi, B. Riedner, G. Garcia-Molina, C. Cirelli, and G. Tononi, "Enhancement of sleep slow waves: underlying mechanisms and practical consequences," Front. Syst. Neurosci., vol. 8, no. October, pp. 1-17, Oct. 2014.

G. Santostasi, R. Malkani, B. Riedner, M. Bellesi, G. Tononi, K. A. Paller, and P. C. Zee, "Phase-locked loop for precisely timed acoustic stimulation during sleep," J. Neurosci. Methods, vol. 259, No. 2016, pp. 101-114, 2016.

G. Garcia-Molina, T. Tsoneva, J. Jasko, B. Steele, A. Aquino, K. Baehr, S. Pastoor, S. Pfundtner, L. Ostrowski, B. Miller, N. Papas, B. Riedner, G. Tononi, and D. P. White, "Closed-loop system to enhance slow-wave activity," J. Neural Eng., vol. 15, No. 6, pp. 1-11, 2018.

International Search Report and Written Opinion, International Application No. PCT/EP2020/081520, dated Feb. 12, 2021.

Garcia-Molina, G. et al., "Hybrid in-phase and continuous auditory stimulation significantly enhances slow wave activity during sleep", 2019 41st Annual International Conference of the IEEE Engineering in Medicine and Biology Society, Jul. 2019.

* cited by examiner

METHOD TO PREDICT THE SLOW-WAVE RESPONSE

CROSS-REFERENCE TO PRIOR APPLICATIONS

This application claims the benefit of U.S. Provisional Application No. 62/933,727, filed on 11 Nov. 2019. This application is hereby incorporated by reference herein.

BACKGROUND

1. Field

The present disclosure pertains to a system and method for delivering sensory stimulation to a subject during a sleep session.

2. Description of the Related Art

Systems for monitoring sleep and delivering sensory stimulation to subjects during sleep are known. Electroencephalogram (EEG) sensor-based sleep monitoring and sensory stimulation systems are known. However, in order to determine if a subject responds to the sensory stimulation and to adjust stimulation parameters, conventional systems require multiple sleep sessions.

SUMMARY

It would be advantageous to determine the effect of sensory stimulation delivered to a subject (e.g., determine whether the subject will respond to the stimulation) during a single sleep session. The system may adjust stimulation parameters in order to alter the effect of the sensory stimulation.

Accordingly, one or more aspects of the present disclosure relate to a system configured to deliver sensory stimulation to a subject during a sleep session. The system comprises one or more sensors, one or more sensory stimulators, one or more processors, and/or other components. The one or more sensors are configured to generate output signals conveying information related to brain activity of the subject during the sleep session. The one or more sensory stimulators are configured to provide the sensory stimulation to the subject during the sleep session. The one or more processors are coupled to the one or more sensors and the one or more sensory stimulators. The one or more processors are configured by machine-readable instructions. The one or more processors are configured to control the one or more sensory stimulators based on stimulation parameters.

In some embodiments, the one or more sensors comprise one or more electroencephalogram (EEG) electrodes configured to generate the information related to brain activity. In some embodiments, the one or more processors are further configured to detect deep non-rapid eye movement (NREM) sleep (also referred to as N3 sleep or S4 in the older sleep stage nomenclature) in the subject. In some embodiments, the one or more processors are configured to determine that the subject has remained in deep NREM sleep for a continuous threshold amount of time during the sleep session.

In some embodiments, detecting deep NREM sleep comprises causing a neural network to be trained based on the information related to the brain activity of the subject, as captured by the EEG electrodes. In some embodiments, based on the output signals, the trained neural network may determine periods when the subject is experiencing deep NREM sleep during the sleep session. The trained neural network comprises an input layer, an output layer, and one or more intermediate layers between the input layer and the output layer.

In some embodiments, the one or more processors are configured such that, once deep NREM sleep is detected, the processors apply stimulation to the subject in blocks of repeating stimulations. In some embodiments, the repeating stimulations may be repeating vibrations, repeating light pulses, and/or other repeating stimulations. In some embodiments, the blocks are separated from one another by an inter-block interval and the repeating stimulations are separated from one another by an intra-block interval. In some embodiments, the inter-block interval is longer than the intra-block interval. In some embodiments, the inter-block interval may have a certain length (e.g., over 3 seconds or some other length). In some embodiments, the intra-block interval may have a certain length that is shorter than the length of the inter-block interval (e.g., 0.1-2 seconds or some other length). These examples are not intended to be limiting, and the lengths may vary.

In some embodiments, the one or more processors are configured to detect unstimulated slow wave activity in the subject during the sleep session. In some embodiments, the unstimulated slow wave activity comprises slow wave activity in the subject during the inter-block interval. The one or more processors are configured to detect stimulated slow wave activity in the subject during the sleep session. In some embodiments, the stimulated slow wave activity comprises slow wave activity in the subject during the blocks of repeating stimulations (i.e., repeating vibrations and/or repeating pulses). The one or more processors may compare the stimulated slow wave activity to the unstimulated slow wave activity. Based on the comparison, the one or more processors may update stimulation parameters of the stimulation.

In some embodiments, the one or more processors are configured to control the sensory stimulators based on the updated stimulation parameters. In some embodiments, the one or more processors may cause the sensory stimulators to provide a subsequent block of stimulations to the subject according to the updated parameters. The one or more processors may then detect and compare unstimulated slow wave activity and stimulated slow wave activity for the subsequent block based on the updated stimulation parameters. In some embodiments, the one or more processors may repeat these steps until the stimulated slow wave activity is significantly higher than the unstimulated slow wave activity. To determine if the stimulated slow wave activity is significantly higher than the unstimulated slow wave activity, the one or more processors may compare the difference between the unstimulated slow wave activity and the stimulated slow wave activity to a threshold. In some embodiments, the threshold is determined based upon a minimum difference for indicating effectiveness of the stimulation.

In some embodiments, once the difference between the stimulated and unstimulated slow wave activity breaches the threshold, the one or more processors may cause the stimulators to deliver continuous stimulation to the subject according to the most recently updated stimulation parameters. In some embodiments, the threshold may represent a minimum difference between the stimulated and unstimulated slow wave activity to indicate effectiveness of the stimulation.

In some embodiments, the one or more sensory stimulators are configured such that the sensory stimulation comprises audible tones. In some embodiments, the one or more sensory stimulators are configured such that the sensory stimulation comprises haptic vibrations. In some embodiments, the one or more sensory stimulators are configured such that the sensory stimulation comprises light pulses. The one or more processors are configured such that updating stimulation parameters of the stimulation based on the comparison of the stimulated slow wave activity to the unstimulated slow wave activity comprises: changing a duration of each stimulation, a duration of the inter-block interval, a duration of the intra-block interval, a number of stimulations, an intensity of the stimulation, and/or a stimulation frequency; and/or causing the one or more sensory stimulators to modulate the stimulation parameters.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
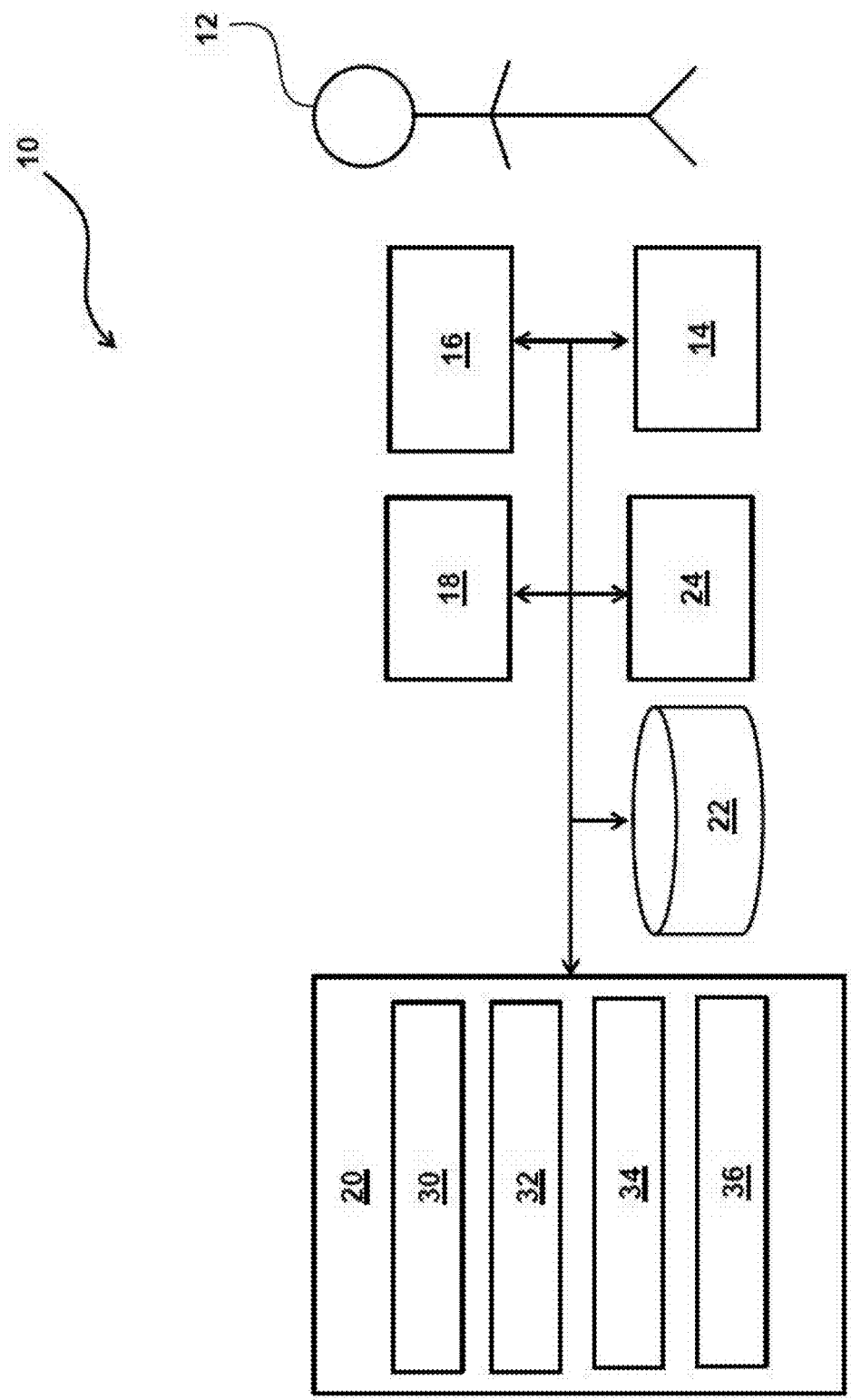
FIG. 1 is a schematic illustration of a system configured to deliver sensory stimulation to a subject during a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to deliver sensory stimulation to a subject 12 during a sleep session. System 10 is configured to facilitate delivery of sensory stimulation to subject 12 to determine if subject 12 responds to sensory stimulation, to update stimulation parameters, and/or for other purposes. System 10 is configured such that sensory stimulation including auditory, haptic, light, and/or other stimulation is delivered during sleep. In some embodiments, the stimulation is only delivered to the subject when processors in system 10 (described below) have determined that subject 12 is in deep NREM sleep. In some embodiments, system 10 delivers stimulation to subject 12 in blocks of repeating stimulations (e.g., repeating vibrations and/or repeating light pulses). As described herein, the one or more processors may compare stimulated slow wave activity in subject 12 (i.e., during a block stimulation) to unstimulated slow wave activity in subject 12 (i.e., between block stimulations or before the block stimulation). The comparison indicates the effect of the stimulation on subject 12. The one or more processors may update the stimulation parameters based on the comparison. In some embodiments, system 10 is configured to repeat the steps until the difference between the stimulated and unstimulated slow wave activities breaches a threshold. Once the difference breaches the threshold, the one or more processors may control the sensory stimulators to deliver continuous stimulation to subject 12 according to the most recently updated stimulation parameters.

Adjusting stimulation parameters is important to ensuring that stimulation during a sleep session is effective for subject 12. The use of block stimulation shortens the necessary adjustment period for this process from several sleep sessions to a portion of a single sleep session. This allows the stimulation process to improve the subject's sleep more quickly and efficiently. System 10 also leverages machine-learning models (e.g., deep neural networks and/or any other supervised machine learning algorithm as described below) for automatic, real-time or near real-time, closed loop, sensor output signals for determining the sleep stage of the subject during the sleep session. As shown in FIG. 1, system 10 includes one or more of a sensor 14, a sensory stimulator 16, external resources 18, a processor 20, electronic storage 22, a subject interface 24, and/or other components. These components are further described below.

Sensor 14 is configured to generate output signals conveying information related to sleep stages of subject 12 during a sleep session. The output signals conveying information related to sleep stages of subject 12 may include information related to brain activity in subject 12. As such, sensor 14 is configured to generate output signals conveying information related to brain activity. In some embodiments, sensor 14 is configured to generate output signals conveying information related to stimulation provided to subject 12 during sleep sessions. In some embodiments, the information in the output signals from sensor 14 is used to control sensory stimulator 16 to provide sensory stimulation to subject 12 (as described below).

Sensor 14 may comprise one or more sensors that generate output signals that convey information related to brain activity in subject 12 directly. For example, sensor 14 may include electroencephalogram (EEG) electrodes configured to detect electrical activity along the scalp of subject 12 resulting from current flows within the brain of subject 12. Sensor 14 may comprise one or more sensors that generate output signals conveying information related to brain activity of subject 12 indirectly. For example, one or more sensors 14 may comprise a heart rate sensor that generates an output based on a heart rate of subject 12 (e.g., sensor 14 may be a heart rate sensor than can be located on the chest of subject 12, and/or be configured as a bracelet on a wrist of subject 12, and/or be located on another limb of subject 12), movement of subject 12 (e.g., sensor 14 may comprise an accelerometer that can be carried on a wearable, such as a bracelet around the wrist and/or ankle of subject 12 such that sleep may be analyzed using actigraphy signals), respiration of subject 12, and/or other characteristics of subject 12.

In some embodiments, sensor 14 may comprise one or more of EEG electrodes, a respiration sensor, a pressure sensor, a vital signs camera, a functional near infra-red sensor (fNIR), a temperature sensor, a microphone and/or other sensors configured to generate output signals related to (e.g., the quantity, frequency, intensity, and/or other characteristics of) the stimulation provided to subject 12, the brain activity of subject 12, and/or other sensors. Although sensor 14 is illustrated at a single location near subject 12, this is not intended to be limiting. Sensor 14 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

In FIG. 1, sensor 14, sensory stimulator 16, processor 20, electronic storage 22, and subject interface 24 are shown as separate entities. This is not intended to be limiting. Some and/or all of the components of system 10 and/or other components may be grouped into one or more singular devices. For example, these and/or other components may be included in a headset 201 and/or other garments worn by subject 12. Other garments may include a cap, vest, bracelet, and/or other garment. Headset 201 and/or other garments may include, for example, sensing electrodes, a reference electrode, one or more devices associated with an EEG, means to deliver auditory stimulation (e.g., a wired and/or wireless audio device and/or other devices), and one or more audio speakers. In some embodiments, headset 201 and/or other garments may comprise means to delivery visual, somatosensory, electric, magnetic, and/or other stimulation to the subject. In this example, the audio speakers may be located in and/or near the ears of subject 12 and/or in other locations. The reference electrode may be located behind the ear of subject 12, and/or in other locations. In this example, the sensing electrodes may be configured to generate output signals conveying information related to brain activity of subject 12, and/or other information. The output signals may be transmitted to a processor (e.g., processor 20 shown in FIG. 1), a computing device (e.g., a bedside laptop) which may or may not include the processor, and/or other devices wirelessly and/or via wires. In this example, acoustic stimulation may be delivered to subject 12 via the wireless audio device and/or speakers. In this example, the sensing electrodes, the reference electrode, and the EEG devices may be represented, for example, by sensor 14 in FIG. 1. The wireless audio device and the speakers may be represented, for example, by sensory stimulator 16 shown in FIG. 1. In this example, a computing device may include processor 20, electronic storage 22, subject interface 24, and/or other components of system 10 shown in FIG. 1.

Stimulator 16 is configured to provide sensory stimulation to subject 12. Sensory stimulator 16 is configured to provide auditory, visual, somatosensory, electric, magnetic, and/or sensory stimulation to subject 12 prior to a sleep session, during a sleep session, and/or at other times. In some embodiments, a sleep session may comprise any period of time when subject 12 is sleeping and/or attempting to sleep. Sleep sessions may include nights of sleep, naps, and/or other sleeps sessions. For example, sensory stimulator 16 may be configured to provide stimuli to subject 12 during a sleep session to enhance EEG signals during deep NREM sleep in subject 12, and/or for other purposes.

Sensory stimulator 16 is configured to affect deep NREM sleep in subject 12 through non-invasive brain stimulation and/or other methods. Sensory stimulator 16 may be configured to affect deep NREM sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. The sensory stimulation may have an intensity, a timing, and/or other characteristics. For example, acoustic tones may be provided to subject 12 to affect deep NREM sleep in subject 12. The acoustic tones may include one or more series of tones of a determined length separated from each other by an inter-tone interval. The volume (e.g., the intensity) of individual tones may be modulated based on various factors (as described herein). The length of individual tones (e.g., the timing) and/or the inter tone interval (i.e., intra-block interval) may also be adjusted. The pitch and tone may also be adjusted. In some embodiments, the stimulation may be delivered to the subject in blocks. In the example of auditory stimulation, each block stimulation has 15 tones. In this example, each tone is in the form of 50-millisecond long tone (e.g., a pink noise tone, which has frequency limits of 500 Hz to 5 KHz). In some embodiments, the duration of each individual stimulation may fall within a range of 10-100 milliseconds (or another duration range). The inter-block interval may be 15 seconds and the intra-block interval (i.e., interval between tones) may be 1 second. In some embodiments, the default volume of the stimulation may be 20 dB. This example is not intended to be limiting, and the stimulation parameters may vary.

Examples of sensory stimulator 16 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to subject 12 (e.g., as described below).

External resources 18 include sources of information (e.g., databases, websites, etc.), external entities participating with system 10 (e.g., one or more the external sleep monitoring devices, a medical records system of a health care provider, etc.), and/or other resources. In some embodiments, external resources 18 include components that facilitate communication of information, one or more servers outside of system 10, a network (e.g., the internet), electronic storage, equipment related to Wi-Fi technology, equipment related to Bluetooth® technology, data entry devices, sensors, scanners, computing devices associated with individual subjects, and/or other resources. In some implementations, some or all of the functionality attributed herein to external resources 18 may be provided by resources included in system 10. External resources 18 may be configured to communicate with processor 20, subject interface 24, sensor 14, electronic storage 22, sensory stimulator 16, and/or other components of system 10 via wired and/or wireless connections, via a network (e.g., a local area network and/or the internet), via cellular technology, via Wi-Fi technology, and/or via other resources.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, subject interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical subject interfaces configured to facilitate subject interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of an information component 30, a model component 32, a control component 34, a modulation component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Information component 30 is configured to determine one or more brain activity parameters of subject 12, and/or other information. The brain activity parameters are determined based on the output signals from sensor 14 and/or other information. The brain activity parameters indicate depth of sleep in subject 12. In some embodiments, the information in the output signals related to brain activity indicates sleep depth over time. In some embodiments, the information indicating sleep depth over time is or includes information related to deep NREM sleep in subject 12.

In some embodiments, the information indicating sleep depth over time may be indicative of other sleep stages of subject 12. For example, the sleep stages of subject 12 may be associated with deep NREM sleep, rapid eye movement (REM) sleep, and/or other sleep. Deep NREM sleep may be stage N3, and/or other deep sleep stages. In some embodiments, the sleep stages of subject 12 may be one or more of stage S1, S2, S3, or S4. In some embodiments, NREM stage 2 and/or 3 (and/or S3 and/or S4) may be slow wave (e.g., deep) sleep. In some embodiments, the information that indicates sleep depth over time is and/or is related to one or more additional brain activity parameters.

In some embodiments, the information related to brain activity that indicates sleep depth over time is and/or includes EEG information and/or other information generated during sleep sessions of subject 12 and/or at other times. In some embodiments, brain activity parameters may be determined based on the EEG information and/or other information. In some embodiments, the brain activity parameters may be determined by information component 30 and/or other components of system 10. In some embodiments, the brain activity parameters may be previously determined and be part of the historical sleep stage information obtained from external resources 18 (described below). In some embodiments, the one or more brain activity parameters are and/or are related to a frequency, amplitude, phase, presence of specific sleep patterns such as eye movements, ponto-geniculo-occipital (PGO) wave, slow wave, and/or other characteristics of an EEG signal. In some embodiments, the one or more brain activity parameters are determined based on the frequency, amplitude, and/or other characteristics of the EEG signal. In some embodiments, the determined brain activity parameters and/or the characteristics of the EEG may be and/or indicate sleep stages that correspond to the deep NREM sleep stage described above.

Information component 30 is configured to obtain historical sleep stage information. In some embodiments, the historical sleep stage information is for subject 12 and/or other subjects. The historical sleep stage information is related to brain activity, and/or other physiological of the population of subjects and/or subject 12 that indicates sleep stages over time during previous sleep sessions of the population of subjects and/or subject 12. The historical sleep stage information is related to sleep stages and/or other brain parameters of the population of subjects and/or subject 12 during corresponding sleep sessions, and/or other information.

In some embodiments, information component 30 is configured to obtain the historical sleep stage information electronically from external resources 18, electronic storage 22, and/or other sources of information. In some embodiments, obtaining the historical sleep stage information electronically from external resources 18, electronic storage 22, and/or other sources of information comprises querying one more databases and/or servers; uploading information and/or downloading information, facilitating subject input, sending and/or receiving emails, sending and/or receiving text messages, and/or sending and/or receiving other communications, and/or other obtaining operations. In some embodiments, information component 30 is configured to aggregate information from various sources (e.g., one or more of the external resources 18 described above, electronic storage 22, etc.), arrange the information in one or more electronic databases (e.g., electronic storage 22, and/or other electronic databases), normalize the information based on one or more features of the historical sleep stage information (e.g., length of sleep sessions, number of sleep sessions, etc.) and/or perform other operations.

Model component 32 is configured such that a trained neural network and/or any other supervised machine learning algorithms are caused to detect deep NREM sleep in subject 12. In some embodiments, this may be and/or include determining periods when subject 12 is experiencing deep NREM sleep during the sleep session and/or other operations. The determined deep NREM sleep, and/or timing, indicates whether subject 12 is in deep NREM sleep for stimulation and/or other information. By way of a non-limiting example, a trained neural network may be caused to indicate determine deep sleep stages and/or timing of the deep sleep stages for the subject based on the output signals (e.g., using the information in the output signals as input for the model) and/or other information. In some embodiments, model component 32 is configured to provide the information in the output signals to the neural network in temporal sets that correspond to individual periods during the sleep session. In some embodiments, model component 32 is configured to cause the trained neural network to output the determined sleep stages of deep NREM sleep for subject 12 during the sleep session based on the temporal sets of information. (The functionality of model component 32 is further discussed below relative to FIG. 2-3.)

As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function that combines the values of all its inputs together. In some embodiments, each connection (or the neural unit itself) may have a threshold function such that a signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free flowing, with connections interacting in a more chaotic and complex fashion.

A trained neural network may comprise one or more intermediate or hidden layers. The intermediate layers of the trained neural network include one or more convolutional layers, one or more recurrent layers, and/or other layers of the trained neural network. Individual intermediate layers receive information from another layer as input and generate corresponding outputs. The detected sleep stages of deep NREM sleep are generated based on the information in the output signals from sensor 14 as processed by the layers of the neural network.

Control component 34 is configured to control stimulator 16 to provide stimulation to subject 12 during sleep and/or at other times. Control component 34 is configured to cause sensory stimulator 16 to provide the sensory stimulation to subject 12 during deep NREM sleep to affect deep NREM sleep in subject 12 during a sleep session. Control component 34 is configured to cause sensory stimulator 16 to provide sensory stimulation to subject 12 based on a detected deep NREM sleep stage (e.g., the output from model component 32) and/or other information. Control component 34 is configured to cause sensory stimulator 16 to provide the sensory stimulation to subject 12 based on the detected deep NREM sleep stage and/or other information over time during the sleep session. Control component 34 is configured to cause sensory stimulator 16 to provide sensory stimulation to subject 12 responsive to subject 12 being in, or likely being in, deep NREM sleep for stimulation. For example, control component 34 is configured such that controlling one or more sensory stimulators 16 to provide the sensory stimulation to subject 12 during the deep NREM sleep to affect the deep NREM sleep in subject 12 during the sleep session comprises: determining the periods when subject 12 is experiencing deep NREM sleep, causing one or more sensory stimulators 16 to provide the sensory stimulation to subject 12 during the periods when subject 12 is experiencing deep NREM sleep, and/or causing one or more sensory stimulators 16 to modulate (e.g., as described herein), an amount, a timing, and/or intensity of the sensory stimulation provided to subject 12 based on the one or more values of the one or more intermediate layers. In some embodiments, stimulators 16 are controlled by control component 34 to affect deep NREM sleep through (e.g., peripheral auditory, magnetic, electrical, and/or other) stimulation delivered during deep NREM sleep (as described herein).

In some embodiments, control component 34 is configured to control sensory stimulator 16 to deliver sensory stimulation to subject 12 responsive to model component 32 determining that subject 12 has remained in deep NREM sleep for a continuous threshold amount of time during the sleep session. For example, model component 32 and/or control component 34 may be configured such that on detection of deep NREM sleep, model component 32 starts a (physical or virtual) timer configured to track the time subject 12 spends in deep NREM sleep. Control component 34 is configured to deliver auditory stimulation responsive to the duration that subject 12 spends in continuous deep NREM sleep breaching a predefined duration threshold. In some embodiments, the predefined duration threshold is determined at manufacture of system 10 and/or at other times. In some embodiments, the predefined duration threshold is determined based on information from previous sleep sessions of subject 12 and/or subjects demographically similar to subject 12 (e.g., as described above). In some embodiments, the predefined duration threshold is adjustable via subject interface 24 and/or other adjustment mechanisms.

In some embodiments, the predefined deep NREM sleep duration threshold may be one minute and/or other durations, for example. By way of a non-limiting example, control component 34 may be configured such that auditory stimulation starts once a minute of continuous deep NREM sleep in subject 12 is detected. In some embodiments, once the stimulation begins, control component 34 is configured to control stimulation parameters of the stimulation. Upon detection of a sleep stage transition (e.g., from deep NREM sleep to some other sleep stage), control component 34 is configured to stop stimulation.

Modulation component 36 is configured to cause sensory stimulator 16 to modulate an amount, a timing, and/or intensity of the sensory stimulation. Modulation component 36 is configured to cause sensory stimulator 16 to modulate the amount, timing, and/or intensity of the sensory stimulation based on the brain activity parameters, values output from the intermediate layers of the trained neural network, and/or other information. As an example, sensory stimulator 16 is caused to modulate the timing and/or intensity of the sensory stimulation based on the brain activity parameters, the values output from the convolutional layers, the values output from the recurrent layers, and/or other information. For example, modulation component 36 may be configured such that sensory stimulation is delivered with an intensity that is proportional to a predicted probability value (e.g., an output from an intermediate layer of a neural network) of a particular sleep stage (e.g., deep NREM). In this example, the higher the probability of deep NREM sleep, the more likely the stimulation continues. If sleep micro-arousals are detected and the sleep stage remains in deep NREM, modulation component 36 may be configured such that the intensity of the stimulation is decreased (by for instance five dBs) responsive to individual micro-arousal detections.

Figure 2:
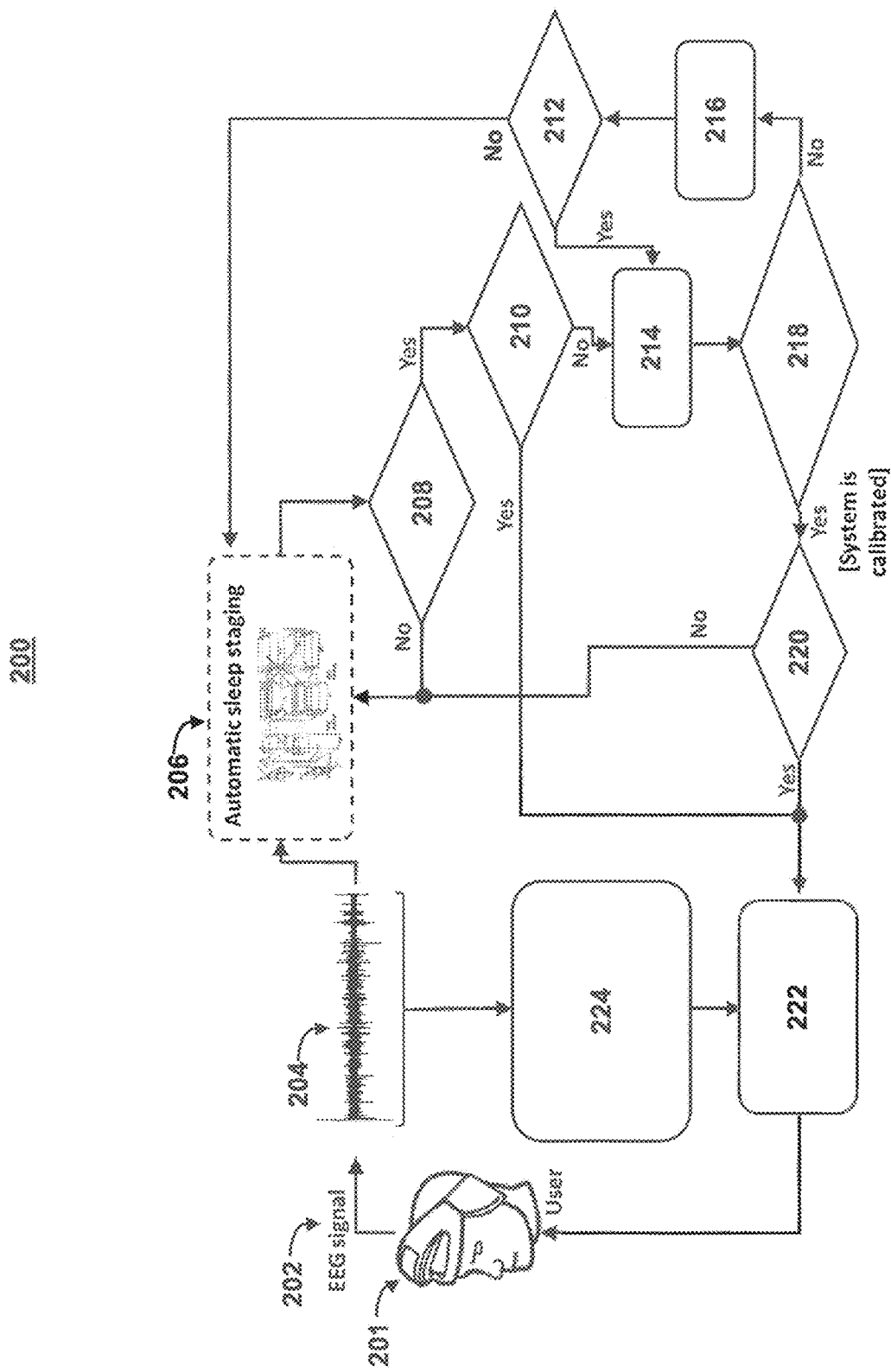
FIG. 2 illustrates several of the operations performed by the system, in accordance with one or more embodiments.

By way of a non-limiting example, FIG. 2 illustrates several of the operations performed by system 10 and described above. In the example shown in process 200 of FIG. 2, an EEG signal 202 is processed and/or otherwise provided (e.g., by information component 30 and model component 32 shown in FIG. 1) to a deep neural network 206 in temporal window 204. Deep neural network 206 detects sleep stages (e.g., N3, N2, N1, REM, and wakefulness). Determination 208 indicates whether the subject is in deep NREM (N3) sleep. If the subject is not in deep NREM sleep, the deep neural network 206 continues to process EEG signal 202 in real time. Deep neural network 206 may determine the sleep stage of the subject as described in relation to FIG. 3. Additionally or alternatively, deep neural network 206 may determine the sleep stage of the subject using methods described in the publication "Recurrent Deep Neural Networks for Real-Time Sleep Stage Classification From Single Channel EEG." *Frontiers in Computational Neuroscience*. Bresch, E., Großekathöfer, U., and Garcia-Molina, G. (2018), which is hereby incorporated by reference in its entirety.

As shown in FIG. 2, responsive to sleep stage determination 208 indicating deep NREM sleep, determination 210 indicates whether the system is calibrated. The calibration may comprise stimulation parameters specifying amount, timing, and/or intensity of the sensory stimulation that is optimal for the subject. In response to determination 210 indicating that the system is not calibrated, block stimulation 214 is applied to the subject during the sleep session. The stimulation parameters for the block stimulation may comprise default amount, timing, and intensity, and/or user-specified amount, timing, and intensity. Block stimulation 214 may occur repeatedly until an enhancement of slow wave activity breaches a threshold 218. In some embodiments, threshold 218 may represent a minimum enhancement of slow wave activity to indicate effectiveness of the stimulation. In some embodiments, the enhancement of slow wave activity may be measured as a difference (e.g., percent difference) between unstimulated slow wave activity and stimulated slow wave activity in the subject during the sleep session. Each time the difference between the stimulated and unstimulated slow wave activity does not breach the threshold 218, the settings 216 are adjusted. If the subject is no longer in deep NREM sleep 212, the process returns to the sleep staging process of the neural network 206. If the subject is still in deep NREM sleep 212, then the block stimulation 214 is applied again. Once the difference breaches the threshold 218, the system has been calibrated.

Once the system is calibrated, if the subject is still in deep NREM sleep 220, the system delivers continuous fixed interval stimulation 222 to the subject. The parameters (e.g., amount, timing, and intensity) of the stimulation are the parameters that were delivered in the block stimulation 214 that breached the threshold 218. The continuous fixed interval stimulation 222 is delivered to the subject for the remainder of the sleep session and in subsequent sleep sessions. The system may continue to extract information 224 about the subject's sleep, such as alpha and beta power, slow wave activity, and sleep depth. The information may be used to adjust or terminate sensory stimulation during each sleep session.

Figure 3:
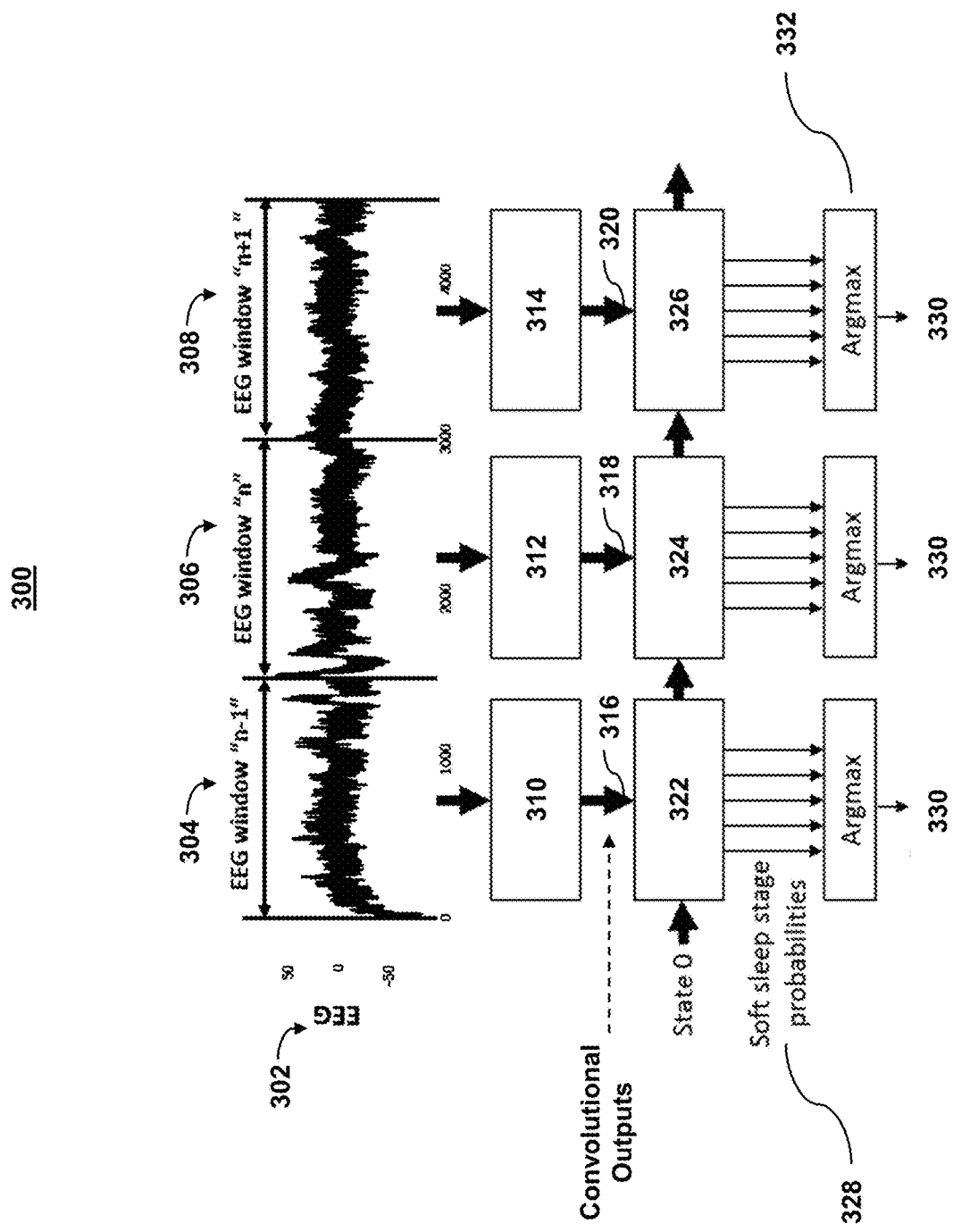
FIG. 3 illustrates example architecture of a deep neural network that is part of the system, in accordance with one or more embodiments.

FIG. 3 illustrates example architecture 300 of a deep neural network (e.g., deep neural network 206 shown in FIG. 2) that is part of system 10 (FIGS. 1 and 2). FIG. 3 illustrates deep neural network architecture 300 for three (unrolled) EEG windows 304, 306, and 308. In some embodiments, windows 304, 306, and 308 may be windows of an EEG signal 302 for pre-defined time periods (e.g., six seconds). Architecture 300 includes convolutional layers 310, 312, and 314, and recurrent layers 322, 324, and 326. As described above, convolutional layers 310, 312, and 314 can be thought of as filters and produce convolution outputs 316, 318, and 320 that are fed to recurrent layers 322, 324, and 326 (LSTM (long short term memory) layers in this example). The output of architecture 300 for individual windows 304, 306, and 308 that are processed are a set of prediction probabilities for individual sleep stages, which are termed "soft output(s)" 328. "Hard" predictions 330 are determined by architecture 300 (model component 32 shown in FIG. 1) by predicting 332 a sleep stage associated with a "soft" output with the highest value (e.g., as described below). The terms "soft" and "hard" are not intended to be limiting but may be helpful to use to describe the operations performed by the system. For example, the term "soft output" may be used, because at this stage, any decision is possible. Indeed, the final decision could depend on post-processing of the soft outputs, for example. "Argmax" in FIG. 3 is an operator that indicates the sleep stage associated with the highest "soft output" (e.g., the highest probability).

For example, a useful property of neural networks is that they can produce probabilities associated with pre-defined sleep stages (e.g., Wake, REM, N1, N2, N3 sleep). Model component 32 (FIG. 1) is configured such that the set of probabilities constitute a so-called soft decision vector, which may be translated into a hard decision by determining which sleep stage is associated with a highest probability value (in a continuum of possible values) relative to other sleep stages. These soft decisions make it possible for system 10 to consider different possible sleep states on a continuum rather than being forced to decide which discrete sleep stage "bucket" particular EEG information fits into (as in prior art systems).

Returning to FIG. 1, model component 32 is configured such that both the values output from convolutional layers, and the soft decision value outputs, are vectors comprising continuous values as opposed to discrete values such as sleep stages. Consequently, convolutional and recurrent (soft decision) value outputs are available to be used by system 10 to modulate the volume of the stimulation when the deep neural network detects occurrences of deep NREM sleep. In addition, as described herein, parameters determined (e.g., by information component 30 shown in FIG. 1) based on the raw sensor output signals (e.g., EEG signals) can be used to modulate stimulation settings.

As described above, modulation component 36 is configured to cause sensory stimulator 16 to modulate an amount, timing, and/or intensity of the sensory stimulation. Modulation component 36 is configured to cause sensory stimulator to modulate the amount, timing, and/or intensity of the sensory stimulation based on the one or more brain activity and/or other parameters, values output from the convolutional and/or recurrent layers of the trained neural network, and/or other information. As an example, the inter-block interval or the intra-block interval of auditory stimulation provided to subject 12 may be adjusted and/or otherwise controlled (e.g., modulated) based on value outputs from the deep neural network such as convolutional layer value outputs and recurrent layer value outputs (e.g., sleep stage (soft) prediction probabilities). In some embodiments, modulation component 36 is configured to cause one or more sensory stimulators 16 to modulate the amount, timing, and/or intensity of the sensory stimulation, wherein the modulation comprises adjusting the inter-block interval, the intra-block interval, the stimulation intensity, and/or the stimulation frequency, responsive to an indication subject 12 is experiencing one or more micro-arousals.

In some embodiments, modulation component 36 is configured to modulate the sensory stimulation based on the brain activity and/or other parameters alone, which may be determined based on the output signals from sensors 14 (e.g., based on a raw EEG signal). In these embodiments, the output of a deep neural network (and/or other machine learning models) continues to be used to detect sleep stages (e.g., as described above). However, the stimulation intensity and timing are instead modulated based on brain activity and/or other parameters or properties determined based on the sensor output signals. In some embodiments, the information in, or determined based on, the sensor output signals can also be combined with intermediate outputs of the network such as output of the convolution layers or the final outputs (soft stages) to modulate intensity and timing (e.g., as described herein).

Figure 4:
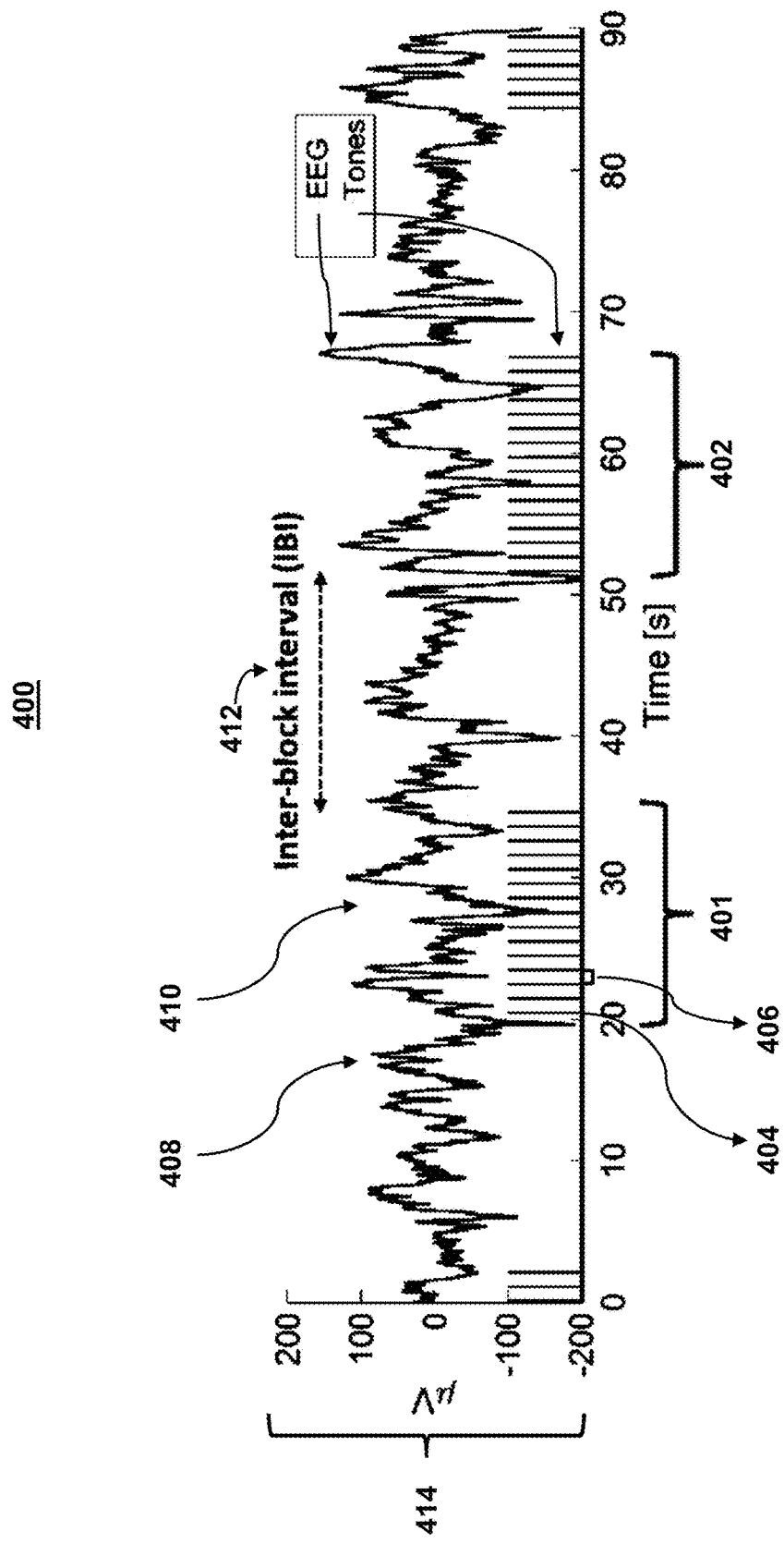
FIG. 4 illustrates delivery of block stimulation to a subject during a sleep session, in accordance with one or more embodiments.

FIG. 4 illustrates delivery of block stimulation to a subject (e.g., 12, as shown in FIG. 1) during a sleep session using a chart 400. As illustrated by chart 400, the EEG data (EEG data 414) indicates deep NREM (N3) sleep. The one or more processors (e.g., 20, as shown in FIG. 1) therefore apply block stimulation (e.g., block 401, according to the process shown in FIG. 2) to the subject during the deep NREM sleep. In some embodiments, the delivery of the first block of stimulations may be synchronized to the up state of the EEG data 414. In some embodiments, the up state of a slow wave comprises a period that is within an interval (e.g., a 300 millisecond interval) from a zero-crossing (e.g., a second zero crossing). In some embodiments, the stimulations may be in the form of auditory vibrations, haptic vibrations, light pulses, and/or other forms of stimulation. The block stimulation may be delivered to the subject (e.g., subject 12 shown in FIG. 1) according to stimulation parameters, such as vibration duration, pulse duration, vibration frequency, pulse frequency, intra-block interval between vibrations, intra-block interval between pulses, inter-block interval, and/or other parameters. As referred to herein, stimulation parameters may comprise any of the aforementioned parameters and/or other parameters.

As shown in FIG. 4, the block stimulation comprises block 401 of fifteen stimulations 404. The number of stimulations per block may vary in other embodiments. Each stimulation 404 within block 401 is delivered at a constant intensity, duration, and frequency, and with a constant intra-block interval 406. As shown in FIG. 4, each stimulation within block 402 is separated from one another by intra-block interval 406 of one second. The duration of intra-block interval 406 may vary in some embodiments. In embodiments in which the stimulation is in the form of auditory vibrations, the pitch may be randomized in the 500-2000 Hz range. In some embodiments, the pitch may be randomized in a wider or narrower range. As shown in FIG. 4, inter-block interval 412 may be fifteen seconds. In some embodiments, inter-block interval 412 may have other durations. In some embodiments, inter-block interval 412 may have the same duration as the blocks of stimulation, a shorter duration, or a longer duration. In embodiments in which the stimulation is in the form of auditory vibrations, the initial intensity may be twenty decibels. In some embodiments, the subject may set the initial intensity.

In some embodiments, the one or more processors (e.g., 20, as shown in FIG. 1) may deliver a first block 401 of stimulations 404 to the subject (e.g., 12, as shown in FIG. 1). The one or more processors may then process the EEG data 414 to determine the effect of the block stimulation on the slow wave activity of the subject. In some embodiments, the one or more processors filter the stimulated slow wave activity 410 through a frequency band (e.g., 0.5-4 Hz), square the filtered data, and/or calculate a running average (and/or other aggregations of the data) for a time period (e.g., four seconds). The one or more processors may then compare the result to an (and/or other aggregation) average of the unstimulated slow wave 408 activity for a time period before the block 401 occurs (e.g., two seconds). In some embodiments, the method of calculating the effect of the stimulation on the subject may vary. Based on the comparison of the processed stimulated slow wave activity data 410 and the processed unstimulated slow wave activity data 408, the one or more processors may determine a difference. The comparison may comprise a difference in slow wave activity levels, a percent difference, and/or any other comparison.

The one or more processors may then compare the difference between the unstimulated slow wave activity 408 and the stimulated slow wave activity 410 to a threshold. In some embodiments, the threshold may represent a minimum difference between the unstimulated slow wave activity 408 and the stimulated slow wave activity 410 to indicate effectiveness of the stimulation. In some embodiments, the threshold may be a forty percent difference between the unstimulated slow wave activity 408 and the stimulated slow wave activity 410. In some embodiments, the threshold may vary.

Figure 5:
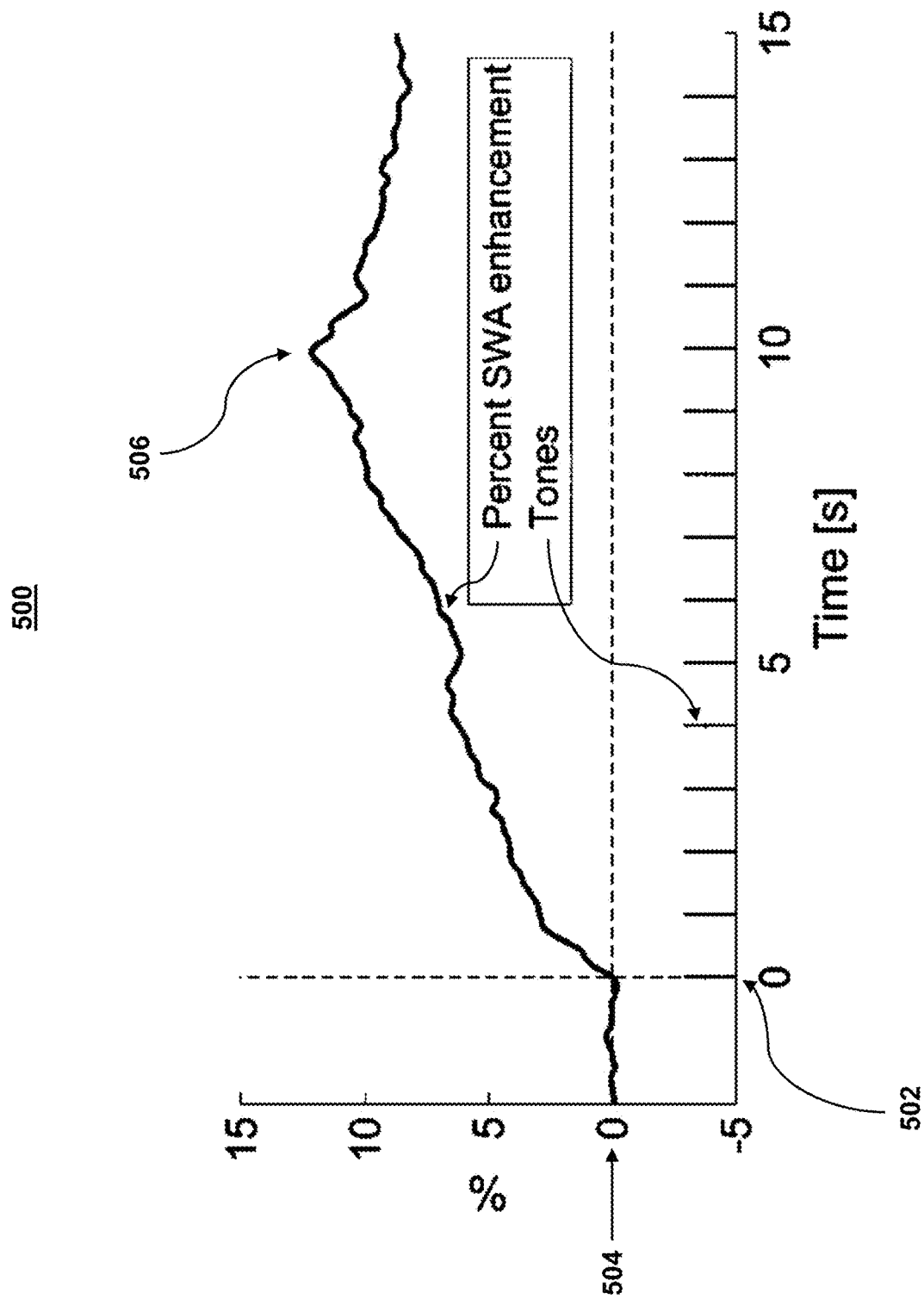
FIG. 5 illustrates an example of a percent difference between stimulated and unstimulated slow wave activity in the subject during the sleep session relative to the beginning of the stimulation, in accordance with one or more embodiments.

FIG. 5 illustrates a graph 500 of an example of a percent difference between stimulated and unstimulated slow wave activity in the subject during an example sleep session relative to the beginning of the stimulation. The percent difference 506 in slow wave activity is zero 504 before the first stimulation 502 begins. Once the stimulation begins (i.e., at time zero), the percent difference 506 increases. The maximum percent difference reached in the 15-stimulation block depicted in FIG. 5 is approximately twelve percent. In this example, if the threshold were forty percent, the percent difference would not breach the threshold.

Returning to FIG. 4, in some embodiments, if the difference between the stimulated and unstimulated slow wave activity levels does not breach the threshold, the one or more processors (e.g., 20, as shown in FIG. 1) may update stimulation parameters (e.g., duration, intensity, frequency, inter-block interval, and/or intra-block interval). In embodiments in which the stimulation is in the form of auditory vibrations, the one or more processors may increase the volume by a given amount (e.g., three decibels). In some embodiments, the one or more processors may increase the intensity of light pulses or haptic vibrations. In some embodiments, the one or more processors may increase the duration of individual stimulations 404, the frequency of stimulations 404, the duration of individual intra-block intervals 406, and/or the duration of individual inter-block intervals 412. In some embodiments, the one or more processors may then deliver the subsequent block 402 to the subject according to the updated stimulation parameters.

In some embodiments, the one or more processors may repeatedly apply blocks of stimulation to the user, perform a comparison between stimulated and unstimulated slow wave activity, compare the difference to the threshold, and update the stimulation parameters until the difference breaches the threshold. With the block stimulation as illustrated in FIG. 4, performing ten rounds of block stimulation requires approximately five minutes. If the first detected deep NREM sleep period is cut short (e.g., due to micro-arousals, transition to another sleep stage, or transition to a wake state), fewer block stimulations may be delivered to the subject (e.g., 12, as shown in FIG. 1). This time requirement is significantly shorter than previous systems, in which multiple adjustments to stimulation settings would require multiple sleep sessions.

In some embodiments, the one or more processors may apply a continuous stimulation to the subject in subsequent sleep sessions, according to the final stimulation parameters of the block stimulation. In some embodiments, the one or more processors may continue to monitor the slow wave activity of the subject in subsequent sleeps sessions.

Figure 6:
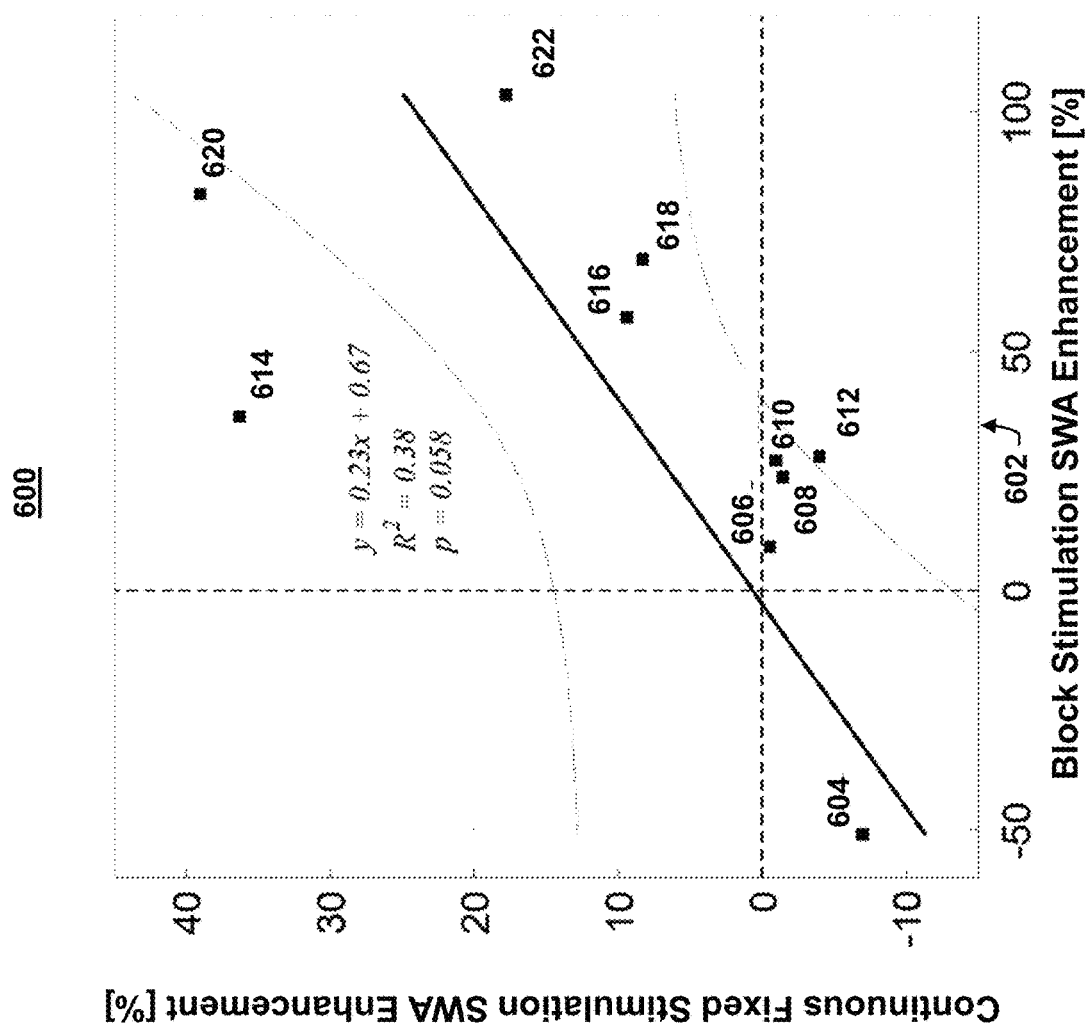
FIG. 6 illustrates an example of a correlation between the effect of block stimulation and the effect of continuous fixed stimulation, in accordance with one or more embodiments.

FIG. 6 illustrates an example of correlation between the effect of block stimulation and continuous fixed stimulation. The horizontal axis of graph 600 illustrates the percent difference (enhancement) between the unstimulated slow wave activity and stimulated slow wave activity for a block stimulation. The vertical axis of graph 600 illustrates the enhancement due to continuous fixed stimulation (e.g., as with the SmartSleep therapy system). Each data point represents a subject, and the position of each data point represents the subject's slow wave activity enhancement due to block stimulation (i.e., horizontal axis) and slow wave activity enhancement due to continuous stimulation (i.e., vertical axis). The positions of the data points indicate that the slow wave activity enhancement due to the block stimulation is significantly correlated with the slow wave activity enhancement associated with the continuous fixed stimulation.

As shown in FIG. 6, the data points indicate that a threshold percent enhancement (e.g., threshold 602) due to block stimulation must be met in order for the subject to respond to the continuous fixed stimulation. As shown in FIG. 6, any data points having block stimulation slow wave activity enhancement that is lower than threshold 602 means that the corresponding subject is not a responder to the continuous fixed stimulation (i.e., the data point falls below zero on the vertical axis). For example, data points 604, 606, 608, 610, and 612 fail to breach the threshold 602 for enhancement due to block stimulation. Data points 604, 606, 608, 610, and 612 therefore all have values below zero for enhancement due to continuous fixed stimulation (i.e., vertical axis). Data points 614, 616, 618, 620, and 622 all breach the threshold 602 for enhancement due to block stimulation. Data points 614, 616, 618, 620, and 622 therefore all have values above zero for enhancement due to continuous fixed stimulation. Further, the slow wave activity enhancement due to the block stimulation is significantly correlated with the slow wave activity enhancement associated with the continuous fixed stimulation for data points 614, 616, 618, 620, and 622. Graph 600 indicates that block stimulation, when applied such that enhancement exceeds a threshold, has a similar effect as continuous fixed stimulation applied with the same parameters.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via subject interface 24 and/or external computing systems (e.g., external resources 18), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

Subject interface 24 is configured to provide an interface between system 10 and subject 12, and/or other subjects through which subject 12 and/or other subjects may provide information to and receive information from system 10. This enables data, cues, results, and/or instructions and any other communicable items, collectively referred to as "information," to be communicated between a subject (e.g., subject 12) and one or more of sensor 14, sensory stimulator 16, external resources 18, processor 20, and/or other components of system 10. For example, a hypnogram, EEG data, deep NREM sleep stage probability, and/or other information may be displayed for subject 12 or other subjects via subject interface 24. As another example, subject interface 24 may be and/or be included in a computing device such as a desktop computer, a laptop computer, a smartphone, a tablet computer, and/or other computing devices. Such computing devices may run one or more electronic applications having graphical subject interfaces configured to provide information to and/or receive information from subjects.

Examples of interface devices suitable for inclusion in subject interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, subject interface 24 comprises a plurality of separate interfaces. In some embodiments, subject interface 24 comprises at least one interface that is provided integrally with processor 20 and/or other components of system 10. In some embodiments, subject interface 24 is configured to communicate wirelessly with processor 20 and/or other components of system 10.

It is to be understood that other communication techniques, either hard-wired or wireless, are also contemplated by the present disclosure as subject interface 24. For example, the present disclosure contemplates that subject interface 24 may be integrated with a removable storage interface provided by electronic storage 22. In this example, information may be loaded into system 10 from removable storage (e.g., a smart card, a flash drive, a removable disk, etc.) that enables the subject(s) to customize the implementation of system 10. Other exemplary input devices and techniques adapted for use with system 10 as subject interface 24 comprise, but are not limited to, an RS-232 port, RF link, an IR link, modem (telephone, cable or other). In short, any technique for communicating information with system 10 is contemplated by the present disclosure as subject interface 24.

Figure 7:
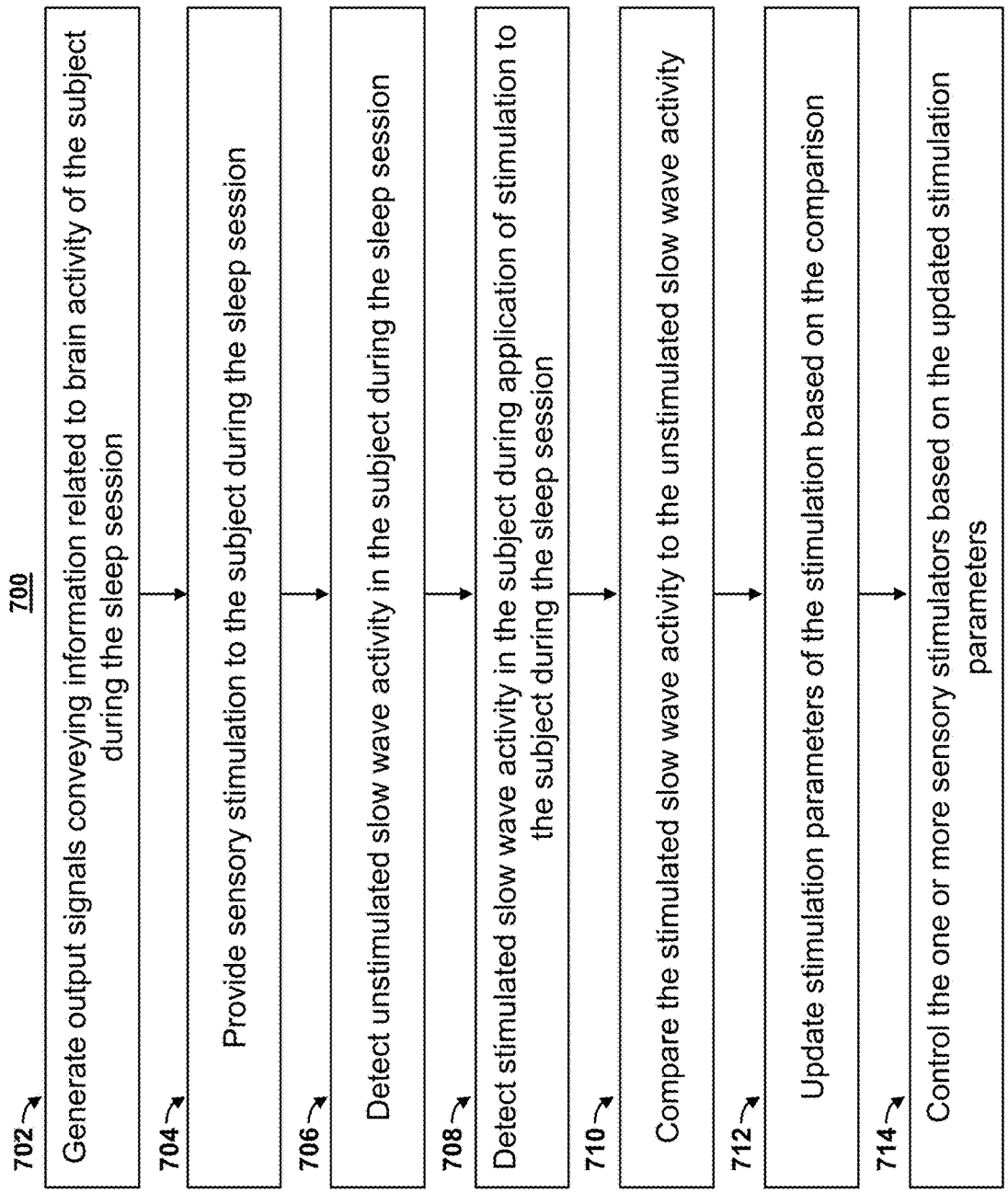
FIG. 7 illustrates a method for delivering sensory stimulation to a subject during a sleep session, in accordance with one or more embodiments.

FIG. 7 illustrates method 700 for delivering sensory stimulation to a subject during a sleep session. The system comprises one or more sensors, one or more sensory stimulators, one or more processors configured by machine-readable instructions, and/or other components. The one or more processors are configured to execute computer program components. The computer program components comprise an information component, a model component, a control component, a modulation component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals conveying information related to brain activity of the subject during the sleep session are generated. The output signals are generated during a sleep session of the subject and/or at other times. In some embodiments, operation 702 is performed by sensors the same as or similar to sensors 14 (shown in FIG. 1 and described herein).

In some embodiments, operation 702 includes providing the information in the output signals to the neural network in temporal sets that correspond to individual periods of time during the sleep session. In some embodiments, operation 710 includes causing the trained neural network to output the detected deep NREM sleep for the subject during the sleep session based on the temporal sets of information. In some embodiments, operation 702 is performed by a processor component the same as or similar to model component 32 (shown in FIG. 1 and described herein).

At an operation 704, sensory stimulation is provided to the subject during the sleep session. The sensory stimulation is applied to the subject in blocks of stimulations with intervals between the stimulations in each block and intervals between the blocks. In some embodiments, the one or more sensory stimulators are caused to provide the sensory stimulation to the subject responsive to a determination that the subject is in deep NREM sleep. In some embodiments, the sensory stimulation may be in the form of auditory vibrations, haptic vibrations, light pulses, and/or another type of sensory stimulation. In some embodiments, operation 704 is performed by a processor component the same as or similar to control component 34 (shown in FIG. 1 and described herein).

At an operation 706, unstimulated slow wave activity in the subject during the sleep session is detected. In some embodiments, the unstimulated slow wave activity may be the slow wave activity for a time period before the beginning of a stimulation (e.g., two seconds before the stimulation). In some embodiments, operation 706 is performed by a processor component the same as or similar to control component 34 (shown in FIG. 1 and described herein).

At an operation 708, stimulated slow wave activity in the subject during the sleep session is detected. The stimulated slow wave activity comprises slow wave activity during application of a block stimulation. In some embodiments, operation 708 is performed by a processor component the same as or similar to control component 34 (shown in FIG. 1 and described herein).

At an operation 710, the stimulated slow wave activity is compared to the unstimulated slow wave activity. The comparison may comprise filtering the stimulated slow wave activity 410 through a frequency band, squaring the filtered data, and/or calculating a running average for a time period. In some embodiments, the unstimulated slow wave activity may comprise an average of the unstimulated slow wave activity for a time period (e.g., two seconds) before the application of the sensory stimulation. The comparison may comprise calculating a difference, percent difference, and/or any other comparison. In some embodiments, operation 710 is performed by a processor component the same as or similar to control component 34 (shown in FIG. 1 and described herein).

At an operation 712, the one or more sensory stimulators are caused to update an amount, a timing, an inter-block interval, an intra-block interval, and/or an intensity of the sensory stimulation based on the comparison of the stimulated slow wave activity to the unstimulated slow wave activity. The one or more sensory stimulators are caused to update the stimulation parameters based on the one or more brain activity parameters and/or values output from the one or more recurrent layers of the trained neural network. In some embodiments, operation 712 is performed by a processor component the same as or similar to modulation component 36 (shown in FIG. 1 and described herein).

In some embodiments, the sensory stimulation comprises audible tones, haptic vibrations, light pulses, and/or other stimulations. Causing the one or more sensory stimulators to update the timing and/or intensity of the sensory stimulation comprises adjusting an inter-block interval, intra-block interval, a number of stimulations, and/or a volume of the stimulations responsive to detection of deep NREM sleep. In some embodiments, the block stimulation is timed to synchronize to the detection of up state of a slow wave in the EEG.

At an operation 714, the one or more sensory stimulators are controlled based on the updated stimulation parameters.

The one or more sensory stimulators may deliver a sensory stimulation to the subject using the updated stimulation parameters (i.e., as updated at operation 712). In some embodiments, operation 714 is performed by a processor component the same as or similar to control component 34 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for delivering stimulation to a subject during a sleep session, the system comprising:
   one or more sensors configured to generate output signals conveying information related to brain activity of the subject during the sleep session;
   one or more sensory stimulators configured to provide sensory stimulation to the subject; and
   one or more processors coupled to the one or more sensors and the one or more sensory stimulators, the one or more processors configured by machine-readable instructions to:
   implement a deep neural network having a number of convolutional layers and a number of recurrent layers, wherein the deep neural network is configured to detect deep NREM sleep in the subject based on the output signals, wherein the number of convolutional layers produce a number of convolution outputs that are fed to the number of recurrent layers, and wherein the number of recurrent layers output a number of recurrent outputs each comprising a prediction probability for each of a plurality of individual sleep stages;
   detect, based on the output signals, unstimulated slow wave activity in the subject during the sleep session while the sensory stimulation is not provided to the subject during the sleep session;
   cause the sensory stimulation to be provided to the subject during the sleep session;
   detect, based on the output signals, stimulated slow wave activity in the subject while the sensory stimulation is provided to the subject during the sleep session;
   compare the stimulated slow wave activity to the unstimulated slow wave activity;
   update stimulation parameters of the sensory stimulation based on the comparison and based on at least one of the convolution outputs and the recurrent outputs; and
   control the one or more sensory stimulators based on the updated stimulation parameters.

2. The system of claim 1, wherein the stimulation is applied to the subject in blocks of repeating vibrations.

3. The system of claim 2, wherein the blocks are separated from one another by an inter-block interval and the repeating vibrations are separated from one another by an intra-block interval, wherein the inter-block interval is longer than the intra-block interval.

4. The system of claim 3, wherein the unstimulated slow wave activity comprises slow wave activity in the subject during the inter-block interval.

5. The system of claim 3, wherein the stimulated slow wave activity comprises slow wave activity in the subject during the blocks of repeating vibrations.

6. The system of claim 3, wherein, to update the stimulation parameters of the stimulation, the one or more processors are further configured to change a duration, an intensity, a vibration frequency, the inter-block interval, or the intra-block interval of the stimulation.

7. The system of claim 3, wherein, to update the stimulation parameters of the stimulation, the one or more processors are further configured to change at least one of the inter-block interval or the intra-block interval of the stimulation based on at least one of the convolution outputs and the recurrent outputs.

8. The system of claim 7, wherein, to update the stimulation parameters, the one or more processors are further configured to change at least one of the inter-block interval or the intra-block interval of the stimulation based on the convolution outputs.

9. The system of claim 7, wherein, to update the stimulation parameters, the one or more processors are further configured to change at least one of the inter-block interval or the intra-block interval of the stimulation based on the recurrent outputs.

10. The system of claim 1, wherein the sensory stimulation comprises auditory vibrations, haptic vibrations, or light pulses.

11. The system of claim 1, wherein the comparison comprises determining a difference between the stimulated slow wave activity and the unstimulated slow wave activity.

12. The system of claim 11, wherein the one or more processors are further configured to:
   compare the difference to a threshold;
   in response to determining that the difference does not breach the threshold, update the stimulation parameters of the stimulation; and
   in response to determining that the difference breaches the threshold, apply the stimulation parameters of the stimulation to a subsequent sleep session.

13. The system of claim 12, wherein the threshold is determined based upon a minimum difference for indicating effectiveness of the stimulation.

14. A method for delivering stimulation to a subject during a sleep session with a system, the system comprising one or more sensors, one or more sensory stimulators configured to provide sensory stimulation to the subject, and one or more processors, the method comprising:
   generating, with the one or more sensors, output signals conveying information related to brain activity of the subject during the sleep session;
   detecting deep NREM sleep in the subject using a deep neural network based on the output signals, the deep neural network having a number of convolutional layers and a number of recurrent layers, wherein the number of convolutional layers produce a number of convolution outputs that are fed to the number of recurrent layers, and wherein the number of recurrent layers output a number of recurrent outputs each comprising a prediction probability for each of a plurality of individual sleep stages;

detecting, with the one or more processors, unstimulated slow wave activity in the subject during the sleep session while the sensory stimulation is not provided to the subject during the sleep session;

causing the sensory stimulation to be provided to the subject during the sleep session;

detecting, with the one or more processors based on the output signals, stimulated slow wave activity in the subject during the sleep session while the sensory stimulation is provided to the subject during the sleep session;

comparing, with the one or more processors, the stimulated slow wave activity to the unstimulated slow wave activity;

updating, with the one or more processors, stimulation parameters based on the comparison and based on at least one of the convolution outputs and the recurrent outputs; and controlling, with the one or more processors, the one or more sensory stimulators based on the updated stimulation parameters.

15. The method of claim 14, wherein the stimulation is applied to the subject in blocks of repeating vibrations.

16. The method of claim 15, wherein the blocks are separated from one another by an inter-block interval and the repeating vibrations are separated from one another by an intra-block interval, wherein the inter-block interval is longer than the intra-block interval.

17. The method of claim 16, wherein the unstimulated slow wave activity comprises slow wave activity in the subject during the inter-block interval.

18. The method of claim 16, wherein the stimulated slow wave activity comprises slow wave activity in the subject during the blocks of repeating vibrations.

19. The method of claim 16, wherein updating the stimulation parameters of the stimulation comprises changing a duration, an intensity, a vibration frequency, the inter-block interval, or the intra-block interval of the stimulation.

20. The method of claim 16, wherein the updating includes changing at least one of the inter-block interval or the intra-block interval of the stimulation based on at least one of the convolution outputs and the recurrent outputs.

21. The method of claim 20, wherein the updating includes changing at least one of the inter-block interval or the intra-block interval of the stimulation based on the convolution outputs and the recurrent outputs.

22. The method of claim 20, wherein the updating includes changing at least one of the inter-block interval or the intra-block interval of the stimulation based on the recurrent outputs.

23. The method of claim 14, wherein the sensory stimulation comprises auditory vibrations, haptic vibrations, or light pulses.

24. The method of claim 14, wherein the comparison comprises determining a difference between the stimulated slow wave activity and the unstimulated slow wave activity.

25. The method of claim 24, further comprising:
comparing the difference to a threshold;
in response to determining that the difference does not breach the threshold, updating the stimulation parameters of the stimulation; and
in response to determining that the difference breaches the threshold, applying the stimulation parameters of the stimulation to a subsequent sleep session.

26. The method of claim 25, wherein the threshold is determined based upon a minimum difference for indicating effectiveness of the stimulation.

* * * * *